United States Patent [19]

Bastian

[11] 4,034,095
[45] July 5, 1977

[54] BENZO[5,6]CYCLOHEPTA[1,2-c]PYRIDINES

[75] Inventor: Jean-Michel Bastian, Therwil, Switzerland

[73] Assignee: Sandoz Ltd., Basel, Switzerland

[22] Filed: Sept. 9, 1976

[21] Appl. No.: 721,835

[30] Foreign Application Priority Data

Sept. 15, 1975 Switzerland .................. 11930/75
Sept. 15, 1975 Switzerland .................. 11931/75
Sept. 15, 1975 Switzerland .................. 11932/75

[52] U.S. Cl. .......................... 424/256; 260/293.54
[51] Int. Cl.² .................................. C07D 221/16
[58] Field of Search ............... 260/293.54; 424/256

[56] References Cited

UNITED STATES PATENTS 3,357,986   12/1967   Villani .................. 260/293

OTHER PUBLICATIONS

Van der Stelt, et al., Arzneim, Forsch. 1972, 22(1), 133–137.

Primary Examiner—Cecilia M. S. Jaisle
Attorney, Agent, or Firm—Gerald D. Sharkin; Robert S. Honor; Timothy G. Rothwell

[57] ABSTRACT

Novel benzo[5,6]cyclohepta[1,2-c]pyridines useful as anti-depressant and anti-cholinergic agents.

29 Claims, No Drawings

BENZO[5,6]CYCLOHEPTA[1,2-C]PYRIDINES

The present invention relates to benzo[5,6]-cyclohepta[1,2-c]pyridines.

More particularly, this invention provides compounds of formula I,

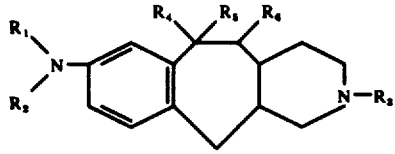

wherein
$R_1$ is hydrogen or alkyl of 1 to 4 carbon atoms,
$R_2$ is hydrogen or alkyl of 1 to 4 carbon atoms,
$R_3$ is hydrogen or alkyl of 1 to 4 carbon atoms, and either
i. $R_4$, $R_5$ and $R_6$ each is hydrogen,
or
ii. $R_4$ and $R_5$ together are oxygen and $R_6$ is hydrogen,
or
iii. $R_4$ and $R_6$ together form a bond and $R_5$ is hydrogen.

The substituent $R_1$ is preferably alkyl, in particular $C_{1-3}$ alkyl, especially methyl or isopropyl.

The subsitutent $R_2$ is preferably hydrogen. When $R_2$ is alkyl, this preferably $C_{1-3}$ alkyl, especially methyl.

$R_3$ may suitably be hydrogen. When $R_3$ is alkyl this is preferably $C_{1-2}$ alkyl, especially methyl.

In one group of compounds, $R_4$, $R_5$ and $R_6$ are each hydrogen. In a second group of compounds, $R_4$ and $R_5$ together are oxygen and $R_6$ is hydrogen. In a third group of compounds, $R_4$ and $R_6$ together form a bond and $R_5$ is hydrogen.

The hydrogen atoms in positions 4a and 11a of the benzo[5,6]cyclohepta[1,2-b]pyridine system can be in either cis or trans configuration to one another. The trans isomers of the compounds of formula I are preferred.

The invention also provides a process for the production of the compounds of formula I, comprising
a. producing a compound of formula Ia,

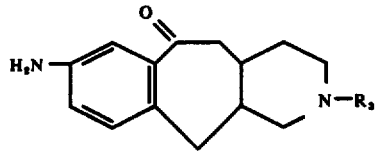

wherein $R_3$ is as previously defined, by reducing a compound of formula II,

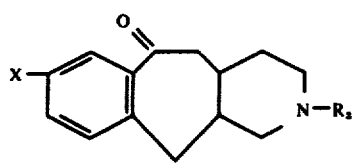

wherein
$R_3$ is as previously defined,
and

X is a nitro group or a radical obtainable by partial reduction of a nitro group, b. producing a compound of formula Ib

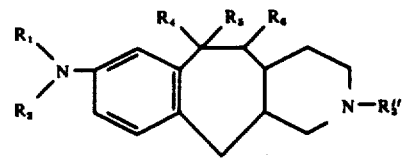

wherein
$R_1$, $R_2$, $R_4$, $R_5$ and $R_6$ are as previously defined,
and
$R_3''$ is alkyl of 1 to 4 carbon atoms,
by alkylating a compound of formula Ic,

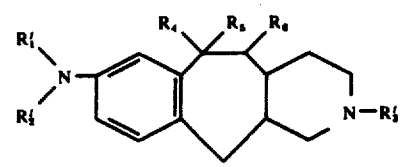

wherein
$R_4$, $R_5$ and $R_6$ are as previously defined,
and
$R_1'$, and $R_2'$ and $R_3'$ each signifies a hydrogen or alkyl of 1 to 4 carbon atoms, provided that at least one of $R_1'$, $R_2'$ and $R_3'$ is hydrogen, c. producing a compound of formula Id,

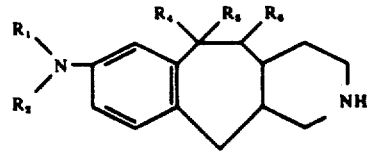

wherein
$R_1$, $R_2$, $R_4$, $R_5$ and $R_6$ are as previously defined,
by solvolytic removal of the group $R_7$ from a compound of formula III,

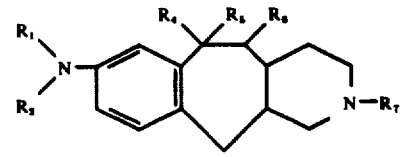

wherein $R_1$, $R_2$, $R_4$, $R_5$ and $R_6$ are as previously defined, and $R_7$ is a group removable by solvolysis, d. producing a compound of formula Ie,

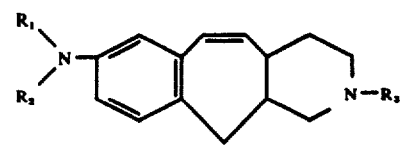

wherein $R_1$, $R_2$ and $R_3$ are as previously defined, by removing water and the radical $R_8$, when this is an acidolytically removable residue, from a compound of formula IV,

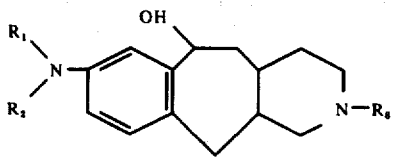

wherein
$R_1$ and $R_2$ are as previously defined, and
$R_8$ is hydrogen, alkyl of 1 to 4 carbon atoms or an acidolytically removable radical, or e. producing a compound of formula I$f$,

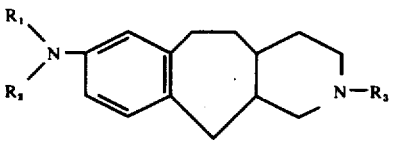

wherein $R_1$, $R_2$ and $R_3$ are as previously defined, by reducing a compound of formula V,

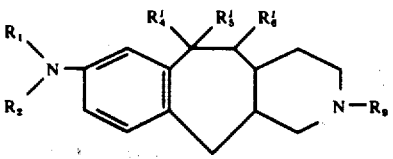

wherein
$R_1$ and $R_2$ are as previously defined,
$R_9$ is hydrogen, alkyl or 1 to 4 carbon atoms, alkoxycarbonyl or aryloxycarbonyl,
and either
i. $R_4'$ and $R_5'$ together are oxygen and $R_6'$ is hydrogen,
or
ii. $R_4'$ and $R_6'$ together form a bond and $R_5'$ is hydrogen.

Process variant a) can be effected by the usual methods for the reduction of aromatic nitro groups to amino groups. The reducing agent and reaction conditions must naturally be so chosen as to avoid reduction of the oxo group in the 6-position. For example, the reduction can be effected by catalytic hydrogenation under mild conditions, particularly using a palladium/charcoal or palladium/barium sulphate catalyst. The catalytic hydrogenation may be effected at standard pressure and at room temperature, particularly in the presence of a solvent which is inert under the reaction conditions, for example, a lower alcohol. The nitro group can also be reduced by a Bechamp reduction using iron. When X is a radical obtainable by partial reduction of a nitro group, the reduction can be effected under the same conditions as those suitable for the nitro compounds.

Process variant b) can be effected by the usual methods for the alkylation of amines. Where $R_3'$ is hydrogen, the piperidino nitrogen is initially alkylated. The type and quantity of alkylation agents and the alkylation conditions can naturally be varied depending on whether or not alkylation of all available positions is required. In general, the alkylation may be effected with compounds $R_{10}Y$, in which $R_{10}$ is alkyl of 1 to 4 carbon atoms, and Y is an acid radical of a reactive ester, preferably halogen or as organic sulphonic acid radical. Where only alkylation of the piperidino nitrogen and/or monoalkylation of the anilino nitrogen is required, alkyl halides, preferably in at most equivalent amounts, are suitably employed, suitably using a halogenated hydrocarbon, acetone or dimethyl formamide as solvent. Preferably, however, the alkylation is in this case effected by reductive reaction with compounds $R_{10}'$-CO-$R_{10}''$, in which $R_{10}'$ and $R_{10}''$ are each independently hydrogen or alkyl and together contain one less carbon atom than the alkyl radical to be introduced. The reductive alkylation may suitably be effected by catalytic hydrogenation in the presence of a palladium catalyst, under mild reaction conditions, for example normal pressure and room temperature. Where dialkylation of the anilino nitrogen is required, a strong alkylation agent, for example a dialkyl sulphate, is suitably used and the reaction is then conveniently effected in the presence of an inorganic base, water, and, optionally, a water-miscible solvent, such as a lower alcohol.

The removal of the radical $R_7$ from the compounds of formula III in process c) may be effected in manner conventional for the solvolytic, in particular hydrolytic, removal of amino protecting groups from heterocyclic amines, for example under conditions conventional for the splitting of urethanes. The radical $R_7$ is suitably an alkoxycarbonyl or aryloxycarbonyl group, in particular a lower alkoxycarbonyl group, such as ethoxycarbonyl, or the nitrile group. The reaction conditions may naturally be varied depending on the nature of $R_7$ but the process is in general suitably effected in acid medium, preferably in the presence of a strong mineral acid, or in alkaline medium, for example in the presence of an inorganic base.

The removal of water in process d) may be effected in known manner, for example by treatment of the compound of formula IV with a suitable dehydration agent, such as a strong acid, acid halide or acid anhydride, and conveniently in the presence of an inert organic solvent. Where $R_8$ is an acidolytically removable group, for example a group described above for $R_7$, in particular the ethoxycarbonyl group, the reaction is effected in the presence of an acid, preferably a strong mineral acid, and conveniently in aqueous or alcoholic solution, the group $R_8$ then being simultaneously removed.

The reduction in process e) may be effected in conventional manner, for example by catalytic hydrogenation. This is conveniently carried out under a hydrogen pressure of 1 to 5 atmospheres, and at a temperature of 10° to 100° C. The catalyst is suitably platinum or palladium. Where, in the starting material V, $R_4'$ and $R_5'$ together signify oxygen, the catalytic hydrogenation is effected in the presence of a strong mineral acid. Alternatively, such compounds may be reduced by the method of Wolf-Kischner, or modifications thereof, or Clemmenson. When $R_9$ is an alkoxy- or aryloxy-carbonyl group, the Wolf-Kischner method, preferably the Huang-Minton variation thereof, is conveniently employed. As will be appreciated, the radical $R_9$ is simultaneously split off when it is an alkoxy- or aryloxycarbonyl radical, to yield products in which $R_3$ is hydrogen.

The resulting compounds of formula I may be isolated and purified using conventional techniques. Where required, free base forms thereof may be converted into acid addition salt forms in conventional manner, and vice versa.

The compounds of formula II may be produced from compounds of formula VI,

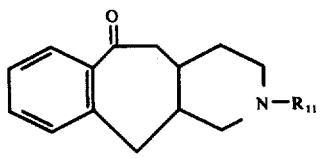

in which $R_{11}$ is alkyl of 1 to 4 carbon atoms, or a solvolytically removable group, by nitration and (to obtain compounds in which $R_3$ is hydrogen) solvolytic removal of the group $R_{11}$ when this is a solvolytically removable group, in conventional manner. The resulting nitro compounds may be partially reduced to obtain compounds in which X is a group obtained by partial reduction of the nitro group. The compounds in which $R_3$ is hydrogen may alternatively be obtained by conventional dimethylation of the compounds in which $R_3$ is methyl.

The compounds of formula VI may be produced from 3-benzyl-4-piperidinoacetic acid (prepared as in Example 1) (optionally cis/trans isomeric mixtures thereof) by alkylation in known manner to introduce $R_{11}$ = alkyl groups or by reaction with $R_{11}$ halides when $R_{11}$ is a solvolytically removable group, for example with a chloroformic acid ester, followed by cyclisation of the resulting product, preferably in the presence of a strong acid condensation agent, for example polyphosphoric acid.

Where the resulting cyclisation product is a cis/trans isomeric mixture, the individual isomers may, if required, be separated in conventional manner.

The compounds of formula VI in which $R_{11}$ is a solvolytically removable group may alternatively be produced from compounds of formula VI in which $R_{11}$ is alkyl, in particular methyl, by reaction with $R_{11}$ halides, where $R_{11}$ is the solvolytically removable group, for example a chloroformic acid ester.

The compounds of formula III may, for example, be produced from compounds of formula I in which $R_3$ is methyl, by replacement of the methyl group with a solvolytically removable group, for example by reaction with a compound $R_7$ Hal, wherein $R_7$ is as defined above and Hal is chlorine or bromine, for example with chloroformic acid esters, for example ethyl chloroformate.

The compounds of formula IV may, for example, be produced by reducing the 6-keto group in a compound of formula VII,

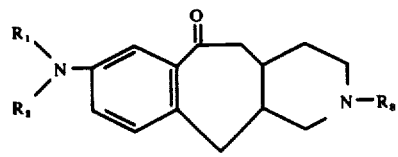

in which $R_1$, $R_2$ and $R_8$ are as defined above, with a complex metal hydride, for example lithium aluminium hydride or sodium borohydride. Where lithium aluminium hydride is employed, any alkoxycarbonyl or aryloxycarbonyl group $R_8$ is simultaneously reduced to methyl. Where, however, sodium borohydride is employed, the group $R_8$ remains unchanged.

As will be appreciated, the compounds of formula VII in which $R_8$ is hydrogen or alkyl are compounds of formula I and may be produced as described above. The compounds of formula VII in which $R_8$ is an acidolytically removable radical be produced from corresponding compounds of formula VI by nitration and, if required, partial reduction of the resulting nitro compounds in manner analogous to that described above for production of compounds II, reduction of the nitro group or partally reduced nitro group in the resulting products, in manner analogous to process (a) described above and, if required, alkylation of the amino group in the resulting products in manner analogous to process (b) described above.

Insofar as the production of the starting materials has not been described, these are either known or may be produced in conventional manner from available materials, or by methods analogous to those described herein.

In the following Examples, all temperatures are in degrees Centigrade and Rf values are determined by thin layer chromatography using silica gel as adsorbent and benzene/ethanol/ammonia (84/15/1) as eluant.

EXAMPLE 1

Trans-8-amino-1,2,3,4,4a,5,11, 11a-octahydro-2-methyl-6H-benzo [5,6]cyclohepta [1,2-c]-pyridin-6-one [process a)]

A solution of 50.0 g of trans-1,2,3,4,4a,5,-11,11a-octahydro-2-methyl-8-nitro-6H-benzo [5,6]cyclohepta [1,2-c]pyridine-6-one in 500 ml of ethanol is hydrogenated in the presence of 2.5 g of palladium (10%) on carbon at normal pressure and room temperature. After absorbtion of the theoretical amount of hydrogen (30 minutes − 1 hour), the catalyst is filtered off and the solution is evaporated to dryness. The title compound is isolated by recrystallisation of the residue from benzene. Melting point: 150°–151°.

The starting material may be produced as follows:

a. 67 g of potassium tert. -butylate are added in portions with ice cooling to a solution of 136 g of phosphonoacetic acid triethyl ester in 125 ml of dimethyl formamide. The reaction mixture is stirred for 1 hour at room temperature, and a solution of 105 g of 3-benzyl-4-oxo-1-piperidine-carboxylic acid ethyl ester in 90 ml of absolute toluene is added to this in drops such that the internal temperature does not exceed 35°. After addition, the reaction mixture is stirred for 18 hours at 70°, cooled to 0°–10°, and 400 ml of 2.5 N hydrochloric acid are added in drops. After diluting with 800 ml of benzene, the mixture is stirred for another 30 minutes, and the organic phase is separated, washed with 10% potassium carbonate solution and water, dried over sodium sulphate and evaporated. The residue is distilled under high vacuum, whereby the 1-ethoxy-carbonyl-3-benzyl-4-piperidylidene-acetic acid ethyl ester distils at 160°–165°/0.005 mm Hg.

b. A solution of 114 g of 1-ethoxycarbonyl-3-benzyl-4-piperidylidene-acetic acid ethyl ester in 120 ml of acetic ester is hydrogenated for 18 hours in the presence of 15 g of 10% palladium on carbon at a pressure of 10 atmospheres and a temperature of 50°. After separating the catalyst, the solvent is evaporated off under reduced pressure. The residual 1-ethoxycarbonyl-3-benzyl-4-piperidine-acetic acid ethyl ester (isomeric mixture) is used for the next stage without purification.

c. A mixture of 114 g of 1-ethoxycarbonyl-3-benzyl-4-piperidine-acetic acid ethyl ester and 2 l of concentrated hydrochloric acid is boiled with stirring for 24 hours. The solution obtained is then evaporated to dryness and then dried under high vacuum for 2–3 hours at 100°. The remaining crude 3-benzyl-4-piperidine-acetic acid hydrochloride (isomeric mixture) is used as such for the next stage. The crude product may be recrystallised from acetone, whereby the α-isomer is obtained with a melting point of 178°–179°.

d. A mixture of 95 g of 3-benzyl-4-piperidine-acetic acid hydrochloride (isomeric mixture), 30 ml of concentrated ammonia solution, 900 ml of 33% formaldehyde solution and 140 ml or 90% formic acid is heated for 18 hours at boiling temperature. After cooling to room temperature and adding 120 ml of concentrated hydrochloric acid, the mixture is evaporated to dryness under reduced pressure and the residue is dried under high vacuum for 5 hours at 100°. The crude 3-benzyl-1-methyl-4-piperidine-acetic acid hydrochloride (isomeric mixture) obtained is further reacted without purification.

e. The crude hydrochloride obtained as above is dissolved in 2.5 l of absolute ethanol, and 12 ml of concentrated sulphuric acid are added. The mixture is heated for 24 hours at boiling temperature, then 12 ml of concentrated sulphuric acid are added again and the mixture is boiled for a further 24 hours. The reaction mixture is concentrated to about 500 ml under reduced pressure, diluted with 2 l of ice water, washed with ether and made alkaline with concentrated caustic soda. The oil which separates out is extracted with ether, the extracts are washed with water, dried over sodium sulphate and evaporated. The residue is distilled under high vacuum, whereby the 3-benzyl-1-methyl-4-piperidine-ethyl acetate (isomeric mixture) distils over at 120°–125°/0.02 mm Hg.

f. 27 g of 3-benzyl-1-methyl-4-piperidine-ethyl acetate are slowly added to 250 g of polyphosphoric acid which has been pre-heated to 100°, then the temperature is increased to 130° and the reaction mixture is stirred for 2 hours at this temperature. After cooling to room temperature, the mixture is poured onto 1 l of water, the solution obtained is washed with ether and made alkaline (pH 9–10) with potassium carbonate. The 1,2,3,4,4a,5,11,-11a-octahydro-2-methyl-6H-benzo[5,6]cyclohepta[1,2-c]-pyridin-6-one which separates as an oil is extracted with ether, the extracts are washed with water, dried over sodium sulphate, evaporated and distilled under high vacuum. Boiling point of the isomeric mixture: 135°–140°/0.05 mm Hg.

Separation of the Isomers:

A solution of 48 g of fumaric acid in 1000 ml of ethanol is mixed with a solution of 95 g of the isomeric mixture in 300 ml of ethanol, and left to stand at room temperature for 48 hours, whereby the trans-1,2,3,4,4a,5,11,11a-octahydro-2-methyl-6H-benzo[5,6]cyclohepta[1,2- c]-pyridin-6-one hydrogen fumarate crystallises out. Melting point: 201°–202° (after recrystallisation from ethanol). The mother liquor which remains after the first crystallisation is evaporated to dryness, then water and methylene chloride are added to the residue, and the mixture is made alkaline by adding caustic soda. After separation of the organic phase, the aqueous phase is shaken out three times with methylene chloride. The combined organic solutions are washed with water, dried over potassium carbonate and evaporated. The residue is dissolved in isopropanol and converted into the hydrochloride with ethereal hydrochloric acid. After standing for several hours at 0°, the hydrochloride of the cis-1,2,3,4,4a,5,11,-11a-octahydro-2-methyl-6H-benzo[5,6]cyclohepta-[1,2-c]pyridin-6-one is filtered off and recrystallised from isopropanol. Melting point: 241–243°.

g. 177 g of trans-1,2,3,4,4a,5,11,11a-octahydro-2-methyl-6H-benzo[5,6]cyclohepta[1,2-c]pyridine-6-one are dissolved at 0° in 460 ml of 98% sulphuric acid. A mixture of 62 ml of 72% nitric acid and 94 ml of 98% sulphuric acid is added in drops over the course of 15 minutes at a temperature of from −10° to −5°. The reaction mixture is then stirred for another 15 minutes at the same temperature, poured onto ice and made alkaline (pH 12–14), with strong cooling, using concentrated caustic soda. The separated product is extracted with methylene chloride, the extracts are washed with water, dried over sodium sulphate and evaporated. The trans-1,2,3,4,4a, 5,11,11a-octahydro-2-methyl-8-nitro-6H-benzo[5,6,]cyclohepta[1,2-c]pyridin-6-one whcich remains as a residue is recrystallised from methylene chloride/hexane. Melting point: 117°–119°.

EXAMPLE 2

Trans-8-amino-1,2,3,4,4a,5,11,11a-octahydro-6H-benzo[5,6]cyclohepta[1,2-c]pyridin-6-one [process a)]

A solution of 8.5 g of trans-1,2,3,4,4a,5,11,11a-octahydro-8-nitro-6H-benzo[5,6]cyclohepta[1,2-c]-pyridin-6-one in 80 ml of glacial acetic acid and 15 ml of water is heated to 90°–95°. 7 g of iron powder are added in portions over the course of 1 hour at this temperature, and another 15 ml of water are added after half of the powder has been added. When this addition is complete, the reaction mixture is stirred for another 30 minutes at the same temperature, then cooled, poured onto ice water and made alkaline (PH 10–12) with potassium carbonate. Methylene chloride is then added to the mixture. The mixture is filtered through diatomaceous earth, the organic phase separated, washed with water, dried over sodium sulphate and evaporated. The title compound which remains as a residue is dissolved in methanol and converted into the hydrogen fumarate form and this is recrystallised from methanol/ether. Decomposition at 240°.

The starting material can be obtained as follows:

a. Trans-2-ethoxycarbonyl-1,2,3,4,4a,5,11,11a-octahydro-6H-benzo[5,6]cyclohepta[1,2-c]pyridine-6-one is obtained by reacting 65.0 g of trans-1,2,3,4,4a,5,11,11a-octahydro-2-methyl-6H-benzo[5,6]cyclohepta[1,2-c]pyridin-6-one with a solution of 94.0 g of chloroformic acid acid-ethyl ester in 200 ml of anhydrous benzene.

b. 59 g of the final product of (a) above are nitrated in manner analogous to Example 1g to yield trans-2-ethoxycarbonyl-1,2,3,4,4a,5,11,11a-octahydro-8-nitro-6H-benzo[5,6]-cyclohepta[1,2-c]pyridin-6-one. M.p. 112°–114°.

c. 7.5 g of the product of step (b ) are split in 40 ml of glacial acetic acid with 20 ml of 48% hydrobromic acid to obtain trans-1,2,3,4,4a,5,11,11a-octahydro-8-nitro-6H-benzo[5,6]cyclohepta[1,2-c]pyridin-6-one, hydrobromide form.

In manner analogous to that of Example 1 or 2, employing appropriate starting materials in approximately equivalent amounts, the compounds of formula Ia indicated in the following Table may be obtained.

| Ex. No. | R₃ | Config. | m.p. |
|---|---|---|---|
| 3 | H | trans | Hydrogen fumarate form, 240° (decomp.) |
| 4 | CH₃ | cis | Hydrochloride form, 289° (decomp.) |

EXAMPLE 5

Trans-1,2,3,4,4a,5,11,11a-octahydro-2-methyl-8-dimethylamino-6H-benzo[5,6]cyclohepta[1,2-c]pyridin-6-one [process b)]

To a mixture of 5.0 g trans-8-amino-1,2,3,4,4a,5,11,-11a-octahydro-2-methyl-6H-benzo[5,6]cyclohepta[1,2-c]pyridin-6-one in 14.5 ml of water and 8.5 g of dimethyl sulphate, are added, dropwise, at 10°, 7.8 g of sodium carbonate. The reaction mixture is slowly warmed to 50° and stirred at this temperature for 1 hour. The mixture is then cooled to 20° and made alkaline with potassium carbonate. The separated product is extracted with methylene chloride and the extract is washed with water, dried over sodium sulphate and evaporated. The residual title compound is dissolved in ethanol and converted to the hydrogennaphthalene disulphonate form, m.p. from 300° (decomp.).

The starting material may be produced in manner analogous to Example 1 by reduction of the nitro group in trans-2-ethoxycarbonyl-1,2,3,4,4a,5,11,11a-octahydro-8-nitro-6H-benzo[5,6]cyclohepta[1,2-c]pyridin-6-one; m.p. of product 132°–133° (recrystallised from benzene/ether).

EXAMPLE 6

Trans-1,2,3,4,4a,5,11,11a-octahydro-8-isopropylamino-2-methyl-6H-benzo[5,6]cyclohepta[1,2-c]pyridin-6-one [process b)]

A solution of 10.0 g of trans-8-amino-1,2,3,4,4a,5,11,11a-octahydro-2-methyl-6H-benzo[5,6]cyclohepta[1,2-c]pyridin-6-one in 200 ml of glacial acetic acid and 55 ml of acetone is hydrogenated in the presence of 5 g of 10% palladium on charcoal at normal pressure and room temperature. After the theoretical amount of hydrogen has been taken up (7-9 hours), the catalyst is filtered off and the solution evaporated to dryness. The residue is taken up in water, made alkaline (pH 12-14) with caustic soda and extracted with methylene chloride. The organic phase is washed with water, dried over sodium sulphate and evaporated. The oily residue of the title compound is converted, in ethanol, to the hydrogen fumarate form, m.p. 233°–235° (decomp.).

In manner analogous to that of Example 5 or 6, employing appropriate starting materials in approximately equivalent amounts, the compounds of formula I indicated in the following Table may be obtained:

| Ex. No. | R₁ | R₂ | R₃ | R₄,R₅,R₆ | Config. 4a/11a | m.p. |
|---|---|---|---|---|---|---|
| 7 | –CH(CH₃)CH₃ | H | CH₃ |  | cis | 268–270° |
| 8 | " | " | " |  | trans | hydrogen maleate: 185° (decomp.) |
| 9 | " | " | " |  | trans | hydrogen fumarate: 210–211° |
| 10 | H | " | " |  | trans | hydrogen fumarate: 208–211° |

EXAMPLE 11:

Trans-8-amino-1,2,3,4,4a,5,11,11a-octahydro-6H-benzo[5,6]cyclohepta[1,2-c]pyridin-6-one [process c]

7 g of trans-2-ethoxycarbonyl-8-amino-1,2,3,4,4a,5,11,11a-octahydro-6H-benzo[5,6]cyclohepta[1,2-c]-pyridin-6-one in 40 ml of glacial acetic acid are mixed with 20 ml of 48% hydrobromic acid and the reaction mixture is boiled for 2 hours and evaporated to dryness. The residue is taken up in water and methylene chloride and made alkaline with caustic soda, and the released base extracted with methylene chloride. The extracts are washed with water, dried over sodium sulphate and evaporated. The residual oil of the title compound is converted, in ethanol, to the hydrogen fumarate form, m.p. from 240° (decomp.).

In manner analogous to that of Example 11, employing appropriate starting materials in approximately equivalent amounts, the compounds of formula Id indicated in the following Table may be obtained.

| Ex. No. | R₁ | R₂ | R₄,R₅,R₆ | Config. 4a/11a | m.p. |
|---|---|---|---|---|---|
| 12 | H | H |  | trans | R_f value : 0.3 |
| 13 | –CH(CH₃)CH₃ | " | " | " | dihydrochloride form 278° (decomp.) |

EXAMPLE 14

Trans-2,3,4,4a,11,11a-hexahydro-8-isopropylamino-2-methyl-1H-benzo[5,6]cyclohepta[1,2-c]pyridine [process d)]

A solution of 15.0 g of trans-2,3,4,4a,5,6,11,11a-octahydro-8-isopropylamino-2-methyl-1H-benzo[5,6]-cyclohepta [1,2-c]pyridin-6-ol in 150 ml of conc. hydrochloric acid is boiled for 45 minutes, evaporated to dryness, and the residue taken up in water, made alkaline (pH 12–14) with 40% caustic soda and extracted with methylene chloride. The organic phase is washed with water, dried over sodium sulphate and evaporated and the residue is mixed with fumaric acid, in ethanol, to form the hydrogen fumarate form of the heading compound, m.p. 210–221°.

The starting material can be produced as follows: To a suspension of 4.1 g of lithium aluminium hydride in 400 ml of anhydrous ether is added, dropwise, over 1 hour, and at room temperature, a solution of 9.5 g of trans-1,2,3,4,4a,5,11,11a-octahydro-8-isopropylamino-2-methyl-6H-benzo[5,6]cyclohepta[1,2-c]pyridin-6-one in 80 ml of anhydrous tetrahydrofuran. The mixture is stirred for 2 hours at room temperature and then under strong cooling at 0° to 5°, mixed first with 80 ml of ethyl acetate and then 50 ml of water. After standing for 15 minutes, the mixture is filtered through diatomaceous earth. The filtrate is evaporated to dryness and the residue is trituratd with ether/petroleum; m.p. of the resulting starting material of Example 14, 169°–171°.

EXAMPLE 15

Trans-8-amino-2,3,4,4a,11,11a-hexahydro-1H-benzo[5,6]cyclohepta[1,2-c]pyridine [process d)]

A mixture of 12.4 g of trans-8-amino-2,3,4,4a,5,6,11,11a-octahydro-6-hydroxy-6H-benzo[5,6]cyclohepta[1,2-c]pyridin-2-carboxylic acid ethyl ester and 125 ml of 48% hydrobromic acid is boiled for 20 minutes to dissolve the substance. The resulting clear solution is cooled to room temperature, made alkaline (pH 14) with caustic soda and shaken with methylene chloride. The organic phase is washed neutral with water, dried over sodium sulphate and evaporated. The heading compound is obtained as an oil, $R_f$-value 0.3.

The starting material can be produced as follows. A solution of 13.2 g of trans-8-amino-1,2,3,4,4a,5,11,-11a-octahydro-2-methyl-6H-benzo[5,6]cyclohepta[1,2-c]pyridin-6-one in 132 ml of ethanol is mixed at 40° with a solution of 1.45 g of sodium borohydride in 4 ml of water and 0.1 ml of water and 0.1 ml of conc. caustic soda and the resulting mixture is stirred for 1 hour at 70°. After addition of 10 ml of methanol, the reaction mixture is boiled for 10 minutes and evaporated to dryness and the residue is dissolved in water and chloroform. After separation of the organic phase, the aqueous phase is extracted with chloroform and the combined organic extracts are washed with water, dried over potassium carbonate and evaporated. The crude product is employed as such in the next step.

In manner analogous to that of Example 14 or 15 employing appropriate starting materials in approximately equivalent amounts, the compounds of formula If, indicated in the following Table, may be obtained:

| Ex. No. | $R_1$ | $R_2$ | $R_3$ | Config. 4a/11a | m.p. |
|---|---|---|---|---|---|
| 16 | H | H | CH₃ | trans | hydrogen fumarate form, 188–189° |
| 17 | H |  | H | " | dihydrochloride form, from 278° (decomp.). |

EXAMPLE 18

Trans-2,3,4,4a,5,6,11,11a-octahydro-8-isopropylamino-2-methyl-1H-benzo[5,6]cyclohepta[1,2-c]pyridine [process e)]

A mixture of 25.0 g of trans-1,2,3,4,4a,5,11,11a-octahydro-8-isopropylamino-2-methyl-6H-benzo[5,6]cyclohepta[1,2-c]pyridin-6-one, 16.0 ml of hydrazine hydrate, 16.0 g of potassium hydroxide and 350 ml of diethylene glycol, is heated first for 1 hour at 150° and then for 3 hours at 200° C, whereby the water formed distils off. The mixture is cooled to room temperature, diluted with water and shaken with methylene chloride. The organic phase is washed neutral with water, dried over sodium sulphate and evaporated, and the residue is reacted in ethanol with the theoretical amount of maleic acid to crystallise out the heading compound in hydrogen maleate form, which is filtered off and recrystallised from ethanol, m.p. from 185° (decomp.).

The compounds of formula I are useful because they possess pharmacological activity in animals. In particular, the compounds possess anti-depressant activity as indicated in standard tests in animals, for example the tetrabenazine antagonism test of G. Stille [Arz. Forsch. 14, 534–7 (1964)] in which an antagonism of ptosis and catalepsy induced in rats by tetrabenazine is observed. The compounds are administered i.p. at from about 10 to about 100 mg/kg of animal body weight. The tetrabenazine is administered i.p. 30 minutes after administration of the compounds at a dosage of 10 mg/kg of animal body weight.

The compounds are therefore useful as anti-depressants, particularly for the treatment of endogenous and reactive depression and retarded depression.

For this use, the dosage will of course vary depending on the compound employed, mode of administration and treatment desired. However, in general, satisfactory results are obtained when administered at a daily dosage of from about 0.05 to 100 mg/kg of animal body weight, conveniently given in divided doses 2 to 4 times a day or in sustained release form. For the larger mammals, the total daily dosage is in the range of from about 5 to about 150 mg, and dosage forms suitable for oral administration comprise from about 1.5 mg to about 125 mg of the compounds admixed with a solid or liquid pharmaceutical carrier or diluent.

The compounds are furthermore useful as anticholinergic agents for the treatment of, for example, Parkinson's disease, as indicated by an induction of a mydriasis effect in mice on i.p. administration of from 15 to 30 mg/kg of animal body weight of the compounds and an antagonism of the tremor caused by oxotremorine in mice on i.p. administration of from 20 to 100 mg/kg of animal body weight of the compounds.

For this usage, the dosage will of course vary depending on the compound employed, mode of administration and treatment desired. However, in general, satisfactory results are obtained when administered at a daily dosage of from about 1 mg to about 100 mg per kg of animal body weight, conveniently given in divided doses 2 to 4 times a day or in sustained release form. For the larger mammals, the total daily dosage is in the range from about 80 to about 150 mg and dosage forms suitable for oral administration comprise from about 20 mg to about 75 mg of the compounds admixed with a solid or liquid pharmaceutical carrier or diluent.

The compounds of formula I may be administered in free base form or in pharmaceutically acceptable acid addition salt form. Such salt forms have the same order of activity as the free base forms. Representative acids for salt formation include inorganic acids, such as hydrochloric acid, and organic acids such as maleic, fumaric and naphthalene-1,5-disulphonic acid.

The compounds may be admixed with conventional pharmaceutically acceptable diluents or carriers and, optionally, other excipients, and administered in such forms as tablets, capsules and solutions, such galenic forms being obtainable in conventional manner.

The compounds of the foregoing Examples exhibit antagonism of tetrabenazine induced ptosis and catalepsy in mice at a dosage of from 10 to about 100 mg/kg of animal body weight i.p.

What is claimed is:

1. A compound of formula

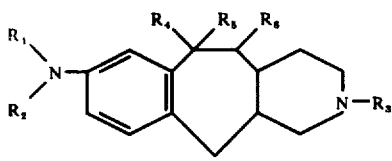

wherein
$R_1$ is hydrogen or alkyl of 1 to 4 carbon atoms,
$R_2$ is hydrogen or alkyl of 1 to 4 carbon atoms,
$R_3$ is hydrogen or alkyl of 1 to 4 carbon atoms, and
either
  i. $R_4$, $R_5$ and $R_6$ each is hydrogen,
or
  ii. $R_4$ and $R_5$ together are oxygen and $R_6$ is hydrogen,
or
  iii. $R_4$ and $R_6$ together form a bond and $R_5$ is hydrogen,
or a pharmaceutically acceptable acid addition salt thereof.

2. The compound of claim 1, which is trans-2,3,4,4a,11,11a-hexahydro-8-isopropylamino-2-methyl-1H-benzo[5,6]cyclohepta[1,2-c]pyridine or a pharmaceutically acceptable acid addition salt thereof.

3. The compound of claim 1, which is trans-2,3,4,4a,5,6,11,11a-octahydro-8-isopropylamino-2-methyl-1H-benzo[5,6]cyclohepta[1,2-c]pyridine.

4. The compound of claim 1 wherein $R_1$ is alkyl.

5. The compound of claim 1 wherein $R_2$ is hydrogen.

6. The compound of claim 1 wherein $R_2$ is alkyl.

7. The compound of claim 1 wherein $R_3$ is hydrogen.

8. The compound of claim 1 wherein $R_3$ is alkyl.

9. The compound of claim 1 wherein each of $R_4$, $R_5$ and $R_6$ is hydrogen.

10. The compound of claim 1 wherein $R_4$ and $R_5$ together are oxygen and $R_6$ is hydrogen.

11. The compound of claim 1 wherein $R_4$ and $R_6$ together form a bond and $R_5$ is hydrogen.

12. The compound of claim 1 in which the 4a, 11a bond is in the trans configuration.

13. The compound of claim 1 which is trans-8-amino-1,2,3,4,4a,5,11,11a-octahydro-2-methyl-6H-benzo[5,6]cyclohepta[1,2-c]pyridin-6-one.

14. The compound of claim 1 which is trans-8-amino-1,2,3,4,4a,5,11,11a-octahydro-6H-benzo[5,6]cyclohepta[1,2-c]pyridin-6-one.

15. The compound of claim 1 wherein each of $R_1$, $R_2$ and $R_6$ is hydrogen, $R_4$ and $R_5$ together are oxygen and $R_3$ is methyl, in cis form.

16. The compound of claim 1 which is trans-1,2,3,4,4a,5,11,11a-octahydro-2-methyl-8-dimethylamino-6H-benzo[5,6]cyclohepta[1,2-c]pyridin-6-one.

17. The compound of claim 1 which is trans-1,2,3,4,4a,5,11,11a-octahydro-8-isopropylamino-2-methyl-6H-benzo[5,6]cyclohepta[1,2-c]pyridin-6-one.

18. The compound of claim 1 wherein $R_1$ is isopropyl, $R_2$ is hydrogen, $R_3$ is methyl, $R_4$ and $R_5$ are together oxygen and $R_6$ is hydrogen, in cis form.

19. The compound of claim 1 wherein $R_1$ is isopropyl, $R_2$ is hydrogen, $R_3$ is methyl and $R_4$, $R_5$ and $R_6$ are each hydrogen, in trans form.

20. The compound of claim 1 wherein $R_1$ is isopropy, $R_2$ is hydrogen, $R_3$ is methyl, $R_4$ and $R_6$ together signify a bond and $R_5$ is hydrogen, in trans form.

21. The compound of claim 1 wherein each of $R_1$, $R_2$ and $R_5$ is hydrogen, $R_3$ is methyl and $R_4$ and $R_6$ together signify a bond, in trans form.

22. The compound of claim 1 wherein each of $R_1$, $R_2$, $R_3$ and $R_5$ is hydrogen, and $R_4$ and $R_6$ together signify a bond, in trans form.

23. The compound of claim 1 wherein $R_1$ is isopropyl, each of $R_2$, $R_3$ and $R_5$ is hydrogen and $R_4$ and $R_6$ together signify a bond, in trans form.

24. The compound of claim 1 which is trans-8-amino-2,3,4,4a,11,11a-hexahydro-1H-benzo[5,6]cyclohepta[1,2-c]pyridine.

25. The compound of claim 1 wherein each of $R_1$, $R_2$, $R_4$, $R_5$ and $R_6$ is hydrogen and $R_3$ is methyl, in trans form.

26. The compound of claim 1 wherein each of $R_1$, $R_3$, $R_4$, $R_5$ and $R_6$ is hydrogen and $R_2$ is isopropyl, in trans form.

27. A method of treating depression which comprises administering to an animal in need of such treatment an effective amount of a compound of claim 1.

28. A method of treating Parkinson's disease which comprises administering to an animal in need of such treatment an effective amount of a compound of claim 1.

29. A pharmaceutical composition for use in treating depression and parkinson's disease comprising a therapeutically effective amount of a compound of claim 1 in association with a pharmaceutical carrier of diluent.

* * * * *